US012676242B2

(12) United States Patent
Krasniatov et al.

(10) Patent No.: US 12,676,242 B2
(45) Date of Patent: Jul. 7, 2026

(54) SYSTEMS AND METHODS FOR ENHANCED OUTLIER DETECTION

(71) Applicant: MedeAnalytics, Inc., Richardson, TX (US)

(72) Inventors: Petro Krasniatov, Poznań (PL); MariBeth Jenkins, Lee's Summit, MO (US); Jeremiah Chronister, McKinney, TX (US); Lillian Phelps, Lutz, FL (US); David Schweppe, Walnut Creek, CA (US)

(73) Assignee: MedeAnalytics, Inc., Richardson, TX (US)

( * ) Notice: Subject to any disclaimer, the term of this patent is extended or adjusted under 35 U.S.C. 154(b) by 6 days.

(21) Appl. No.: 18/612,802

(22) Filed: Mar. 21, 2024

(65) Prior Publication Data

US 2025/0299834 A1     Sep. 25, 2025

(51) Int. Cl.
*G16H 50/00* (2018.01)
*G06Q 40/08* (2012.01)
*G16H 50/70* (2018.01)

(52) U.S. Cl.
CPC ............. *G16H 50/70* (2018.01); *G06Q 40/08* (2013.01)

(58) Field of Classification Search
CPC ............................... G16H 50/70; G06Q 40/08
USPC .......................................................... 705/4
See application file for complete search history.

(56) References Cited

U.S. PATENT DOCUMENTS

| | | | | |
|---|---|---|---|---|
| 7,333,923 B1* | 2/2008 | Yamanishi | ....... | G06Q 10/06395 706/14 |
| 2003/0229519 A1* | 12/2003 | Eidex | .................... | G06Q 40/08 705/2 |
| 2008/0249820 A1* | 10/2008 | Pathria | .................. | G16H 50/70 705/30 |
| 2014/0081652 A1* | 3/2014 | Klindworth | ........ | G06Q 10/0635 705/2 |

* cited by examiner

*Primary Examiner* — Hai Tran
(74) *Attorney, Agent, or Firm* — Sterne, Kessler, Goldstein & Fox P.L.L.C.

(57) ABSTRACT

Disclosed herein are system, apparatus, device, method and/or computer program product embodiments, and/or combinations and sub-combinations thereof, for detecting and displaying healthcare outlier data. Some embodiments involve: receiving a claim including a provider, an illness, a treatment, and a risk score based on the illness and the treatment; updating a metric associated with the provider based on the claim; normalizing the metric using the risk score, the illness, and the treatment; determining that the normalized metric is an outlier by: (1) comparing the normalized metric to a threshold and; (2) determining that the normalized metric is associated with a statistically significant number of claims; in response to determining that the normalized metric is an outlier, presenting an indication of the outlier to a user. In some embodiments, the presenting may further include transmitting an alert to user computing device associated with the user.

20 Claims, 11 Drawing Sheets

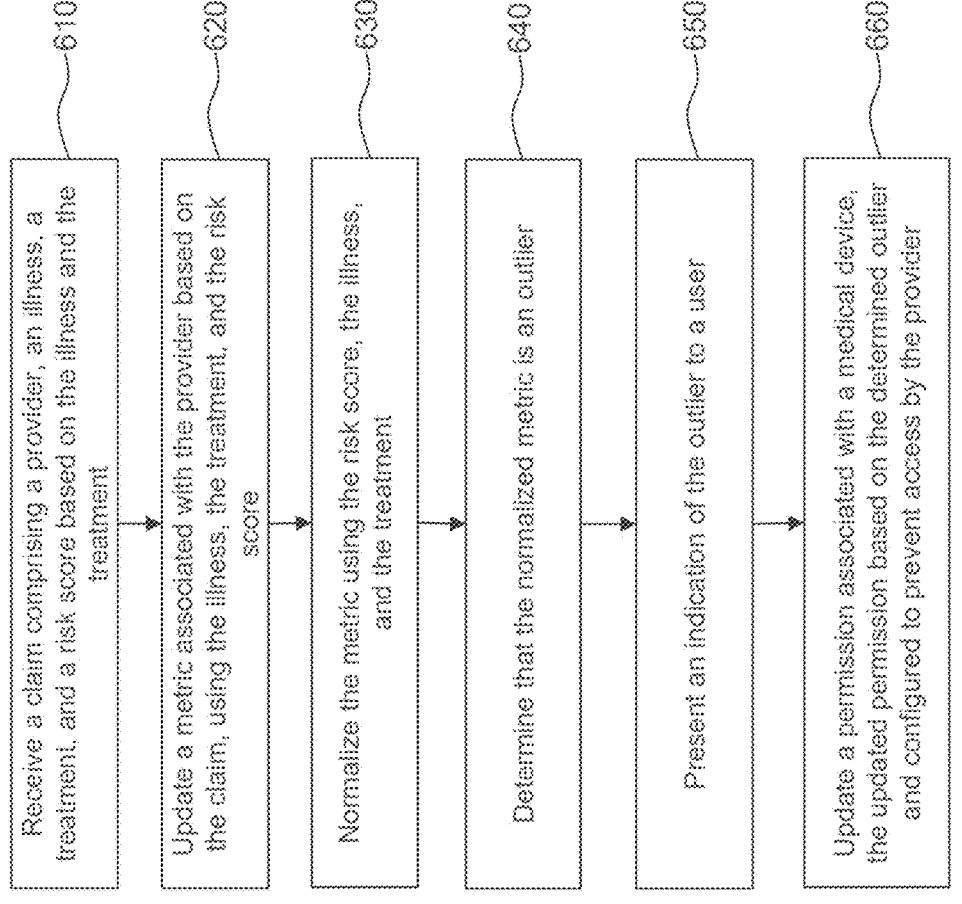

610

Receive a claim comprising a provider, an illness, a treatment, and a risk score based on the illness and the treatment

620

Update a metric associated with the provider based on the claim, using the illness, the treatment, and the risk score

630

Normalize the metric using the risk score, the illness, and the treatment

640

Determine that the normalized metric is an outlier

650

Present an indication of the outlier to a user

660

Update a permission associated with a medical device, the updated permission based on the determined outlier and configured to prevent access by the provider

SYSTEMS AND METHODS FOR ENHANCED OUTLIER DETECTION

BACKGROUND

In large data environments where millions of data points are generated and communicated, it may be difficult to identify trends, determine outliers, and make executive decisions. This problem is even more prevalent in environments such as healthcare. As a result of increased connectivity, healthcare provider networks (e.g., a hospital system) can generate millions of data points based on their provider's acts. This data may be valuable to identify trends and patterns regarding patient illness and treatment. In addition to trend detection, there is a need to identify outliers in order to avoid potentially life-threatening situations. There is also a need to provide real-time controls designed to address and mitigate any effects resulting from the outliers.

BRIEF SUMMARY

Disclosed herein are system, apparatus, device, method and/or computer program product embodiments, and/or combinations and sub-combinations thereof, for detecting and displaying outlier data. Some embodiments relate to a method comprising: receiving a claim comprising a provider, an illness, a treatment, and a risk score based on the illness and the treatment; updating a metric associated with the provider based on the claim; normalizing the metric using the risk score, the illness, and the treatment; determining the normalized metric is an outlier by: (1) comparing the normalized metric to a threshold; and (2) determining that the normalized metric is associated with a statistically significant number of claims; and in response to determining that the normalized metric is an outlier, presenting an indication of the outlier to a user. In some embodiments, the presenting may further include transmitting an alert to user computing device associated with the user.

Some embodiments relate to a system comprising: a memory; and at least one processor coupled to the memory and configured to: receive a claim including a provider, an illness, a treatment, and a risk score based on the illness and the treatment; update a metric associated with the provider based on the claim; normalize the metric using the risk score, the illness, and the treatment; determine that the normalized metric is an outlier by: (1) comparing the normalized metric to a threshold; and (2) determining that the normalized metric is associated with a statistically significant number of claims; and in response to determining that the normalized metric is an outlier, present an indication of the outlier to a user. In some embodiments, the presentation may further include transmitting an alert to user computing device associated with the user.

Some embodiments relate to a non-transitory computer-readable device having instructions stored thereon. When the instructions are executed by at least one computing device, the instructions cause the at least one computing device to perform operations comprising: receiving a claim including a provider, an illness, a treatment, and a risk score based on the illness and the treatment; updating a metric associated with the provider based on the claim; normalizing the metric using the risk score, the illness, and the treatment; determining that the normalized metric is an outlier by: (1) comparing the normalized metric to a threshold; and (2) determining that the normalized metric is associated with a statistically significant number of claims; and in response to determining that the normalized metric is an outlier, presenting an indication of the outlier to a user. In some embodiments, the presenting may further include transmitting an alert to user computing device associated with the user.

BRIEF DESCRIPTION OF THE DRAWINGS

The accompanying drawings are incorporated herein and form a part of the specification.

FIG. 6 is a flowchart illustrating an example process for detecting and displaying healthcare outlier data, according to some embodiments.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, device, method and/or computer program product embodiments, and/or combinations and sub-combinations thereof, for detecting and displaying outlier data. While embodiments are primarily discussed within a healthcare environment, the techniques are generally applicable to other environments in which large quantities of data are analyzed, such as (without limitation) network traffic monitoring, network intrusion detection, and financial trading. Some embodiments may be configured to retrieve and analyze healthcare provider data. Once the data is retrieved, it may be normalized in order to identify trends, outliers, and perform corrective actions. As discussed further below, normalization may involve removing the effect that patient illness has on the metrics. This normalization process is therefore beneficial so that providers may be evenly compared.

After normalization, providers may be compared to identify trends. Trends may be identified, for example, based on the provider's own history, a specialty group the provider belongs to, or an entire provider system (e.g., a hospital, a private practice, etc.). As a result of the comparison, the system may identify outlier metrics. For example, an outlier may be identified when the metric is greater than or less than a predefined threshold. Based on the metric, the system may take various actions. In some embodiments, the system may change the provider's access permissions. For example, the system may detect that the provider is prescribing opioid medications at a rate greater than a threshold. In response, the system may automatically update the provider's permissions so that they may no longer prescribe opioids.

Some embodiments may further provide an application operated by end-user devices. The end-user application may be operated by a user device to view, manage, and otherwise interact with the system. For example, the application may allow users to view metrics, trends, and outliers within the data. Additionally, the system may send alerts or notifications to the application so that users may take corrective action. For example, the application may enable an end-user device to update a provider's permissions based on the detected outlier. In some embodiments, the end-user may determine that the outlier is a false positive and choose to disregard it. In either case, embodiments presented herein enable efficient and accurate outlier detection and response based on real-time data analysis.

Figure 1:
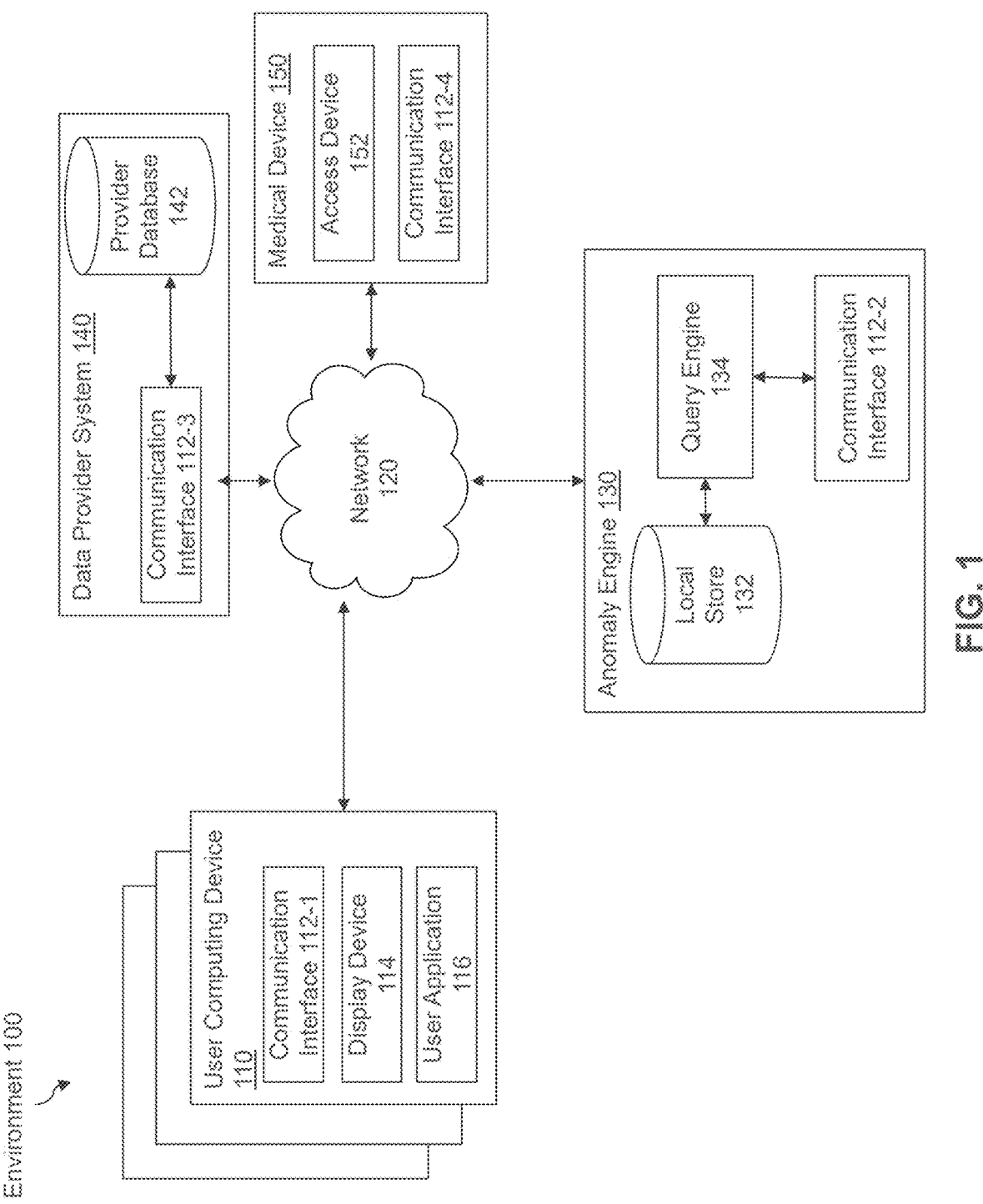
FIG. 1 depicts an exemplary environment for detecting and displaying healthcare outlier data, according to some embodiments.

FIG. 1 depicts an exemplary environment 100 for detecting and displaying outlier data, according to some embodiments. Environment 100 includes user computing device 110, network 120, anomaly engine 130, data provider system 140, and medical device 150.

User computing device 110 may be any entity attempting to communicate with anomaly engine 130. Although a single user computing device 110 is depicted, environment 100 may include multiple user computing devices 110. User computing device 110 may be a computer system such as computer system 700 described with reference to FIG. 7. User computing device 110 may be a client system such as a desktop workstation, laptop or notebook computer, netbook, tablet, smart phone, and/or other computing device that may be using an enterprise computing system.

User computing device 110 includes communication interface 112-1, display device 114, and user application 116. Communication interface 112-1 may be configured to communicate with anomaly engine 130 via network 120. Communication interface 112-1 may comprise any suitable network interface capable of transmitting and receiving data, such as, for example a modem, an Ethernet card, a communications port, or the like. Communication interface 112-1 may be able to transmit data using any wireless transmission standard such as, for example, Wi-Fi, Bluetooth, cellular, or any other suitable wireless transmission. Display device 114 may be configured to display information at user computing device 110. Display device 114 may be configured to receive interactions. An interaction may be, for example, a button press, swipe, touch, click, etc. User application 116 may be an app installed on user computing device 110 that interacts with anomaly engine 130. A user may access, view, and interact with user application 116 via display device 114.

Network 120 may be any type of computer or telecommunications network capable of communicating data, for example, a local area network, a wide-area network (e.g., the Internet), or any combination thereof. The network may include wired and/or wireless segments.

Data provider system 140 may be any entity capable of generating and/or storing data. For example, data provider system 140 may be a hospital, an internet service provider, or a financial institution. Data provider system 140 includes communication interface 112-3 and provider database 142. Data provider system 140 may communicate with anomaly engine 130, via communication interface 112-3, over network 120. Data provider system 140 may be in communication with data store 140 via network 120. Although a single data provider system 140 is depicted, environment 100 may include multiple data provider systems 140.

Data provider system 140 may store data or metrics at provider database 142. For example, if data provider system 140 is a hospital, provider database 142 may include, among others, metrics regarding employees, patients, treatments performed, and insurance claims generated and submitted. Data provider system 140 may automatically send updated metrics to anomaly engine 130. In some embodiments, data provider system 140 may respond to requests from anomaly engine 130 for updated data. For example, anomaly engine 130 may perform a "refresh" operation, requesting updated values for tracked data. Data provider system 140 may transmit the updated values over network 120.

Anomaly engine 130 may be implemented using one or more servers and/or databases. In some embodiments, anomaly engine 130 may be implemented using a computing device such as a desktop workstation, laptop or notebook computer, netbook, tablet, smart phone, and/or other computing device. In some embodiments, anomaly engine 130 may be implemented as an application in an enterprise computing system and/or a cloud-computing system. In some embodiments, anomaly engine 130 may be a computer system such as computer system 700 described with reference to FIG. 7. Although a single anomaly engine 130 is depicted, environment 100 may include multiple anomaly engines 130. If environment 100 includes multiple anomaly engines 130, anomaly engine 130 closest to data provider system 140 may be configured to retrieve data from data provider system 140. Such an architecture reduces network latency associated with retrieving and transmitting data, allowing for faster response to detected outliers.

Anomaly engine 130 includes local store 132, query engine 134, and communication interface 112-2. Local store 132 may be a memory storage device configured to store data from data store 140. In some embodiments, local store 132 may employ one or more databases for storing and organizing data.

Query engine 134 may be configured to retrieve data from data provider system 140 and save it to local store 132. Query engine 134 may communicate, through communication interface 112-2, with data provider system 140 via network 120. In some embodiments, each time query engine 134 obtains a new metric value, it may overwrite the current value at local store 132. This process ensures local store 132 stores the most up to date information as well as reduces the amount of storage required by local store 132. In some embodiments, query engine 134 may be configured to maintain a history of data at local store 132. For example, a data category may be updated once per day, and local store 132 may be configured to keep the last thirty values. In this embodiment, once thirty values are stored at local store 132, query engine 134 may overwrite the oldest value. Storing a limited history of metric values allows local store 132 to remain small while also providing user computing device 110 the benefit of historical data.

Query engine 134 may retrieve data according to an update frequency or schedule. For example, query engine 134 may be configured to retrieve data from data provider system 140 once a week, once a day, once an hour, once per minute, or once per second. In some embodiments, data provider system 140 may automatically send new data to anomaly engine 130 for analysis, which may be performed according to a specified frequency, schedule, or upon detecting changes to particular metric values. In some embodiments, user computing device 110 may set the update frequency or schedule. Anomaly engine 130 may further be configured with a default update frequency (e.g., once per day).

Local store 132 may be organized in any logical configuration. For example, data at local store 132 may be organized by individual providers, specialty groups, or provider systems (e.g., by hospital or private practice). Additional configurations may also include organizing data by municipality such as city, county, or state.

In some embodiments, data retrieved by anomaly engine 130 may be organized into claims. Each claim may include a provider, an illness, a treatment, and a risk score based on the illness and the treatment. A provider may refer to a medical professional such as a physician. An illness may refer to any medical issue and the treatment may refer to any actions taken or medication prescribed to treat the illness. The risk score may be a score calculated based on the severity of patient illness. For example, a patient undergoing open-heart surgery may have a higher risk score than a patient recently diagnosed with diabetes.

Anomaly engine 130 may be configured to group providers. The grouping may occur prior to or after identifying outliers within the retrieved data. In some embodiments, providers may be grouped according to defined specialties (e.g., pediatrics, orthopedic surgery, and cardiology), provider system (e.g., by hospital or private practice), region (e.g., city, state), or by other specified criteria. Anomaly engine 130 may assign a grouping based on the contents of the claim. For example, the claim may include a code or identifier that anomaly engine 130 uses to assign the grouping. In some embodiments, the claim may not include any identifier to assign the grouping. In such a case, anomaly engine 130 may use historical data to assign the grouping. For example, anomaly engine 130 may reference historical data at local store 132 to identify whether the provider has previously been assigned to a group. In some embodiments, anomaly engine 130 may submit a request for an assigned group from data provider system 140.

Grouping providers allows for more precise outlier identification. Specialized providers often treat complex illnesses. Grouping providers by specialty reduces the risk that providers treating simpler patients will contribute to false positive outlier detections. For example, an internal medicine doctor may be associated with zero mortalities, whereas a trauma surgeon may be associated with ten mortalities. Although such a mortality rate may be considered normal within the trauma field, comparing these two providers may increase the chance of the trauma surgeon being labeled an outlier. Grouping providers by specialty greatly reduces the number of false positives detected by anomaly engine 130, increasing the accuracy of detected outliers and allowing the system to make real-time decisions with minimal (if any) user intervention.

In addition to grouping providers, anomaly engine 130 may be configured to normalize data it retrieves from data provider system 140. Anomaly engine 130 may be configured to normalize the data with respect to any category. For example, anomaly engine 130 may be configured to remove the impact that patient health risk (e.g., severity of patient illness) has on certain metrics. Normalization may be required even within groupings. For example, two cardiologists may treat patient populations with differing levels of illness. Therefore, in order to identify outliers between the cardiologists, there is a need to remove any impact caused by the severity of patient illness treated by each respective cardiologist.

Various metrics may be affected by the severity of a patient's illness. For example, sicker patients may require longer time in a hospital compared to healthier patients. If the physicians treating these patients were directly compared, the physician treating sicker patients may be mislabeled an outlier because many metrics (length of stay, cost of treatment, course of treatment, etc.) are tied to the severity of a patient's illness. As will be discussed below, anomaly engine 130 may normalize the data (e.g., eliminate the impact of the severity of patient illness) from the data prior to the comparison, so that the physicians may be more fairly compared. In some embodiments, anomaly engine 130 may be configured to normalize the data using a patient risk score. The patient risk score may be received in a claim from data provider system 140. In some embodiments, anomaly engine 130 may be configured to calculate a risk score based on the information within the claim. Anomaly engine 130 may use information about the patient, their illness, and treatment to calculate the risk score. Risk score calculation may consider any data point such as patient age, sex, height, weight, illness, treatment, illness history, and treatment history.

In some embodiments, removing the severity of patient illness from a selected metric may be performed via a reverse linear regression. This process may involve two primary steps. First, a risk impact coefficient may be calculated. The risk impact coefficient may be an estimate of how much the selected metric may be affected by one unit of change in patient illness severity. In some embodiments, the patient illness severity may be represented by the patient risk score discussed above. The risk impact coefficient may be calculated by dividing the metric value by the patient risk score. Second, the process may calculate a new selected metric value by removing the impact of patient illness severity. In some embodiments, this new metric value is calculated by subtracting from the selected metric value, the product of: (1) the risk impact coefficient calculated above; and (2) the patient risk score. The new selected metric value may then be used to compare providers. Anomaly engine 130 may perform this process for each metric (e.g., data category) received from data provider system 140. This process allows providers to be compared, and outlier metrics to be accurately identified and acted upon.

In some embodiments, anomaly engine 130 may normalize the metric over a specified time window. The specified time window may be any period of time such as the last month, last year, or time between two dates (e.g., Jan. 1, 2023-Jan. 1, 2024). This may be accomplished by using the metric value and patient risk score for the specified time window.

An outlier may be defined in various ways. In some embodiments, a metric greater than or less than a value may indicate an outlier. For example, any claim generated by pediatrics with a length of stay more than five days may be an outlier. In some embodiments, an outlier may be detected based on a metric falling outside a defined range of values. For example, emergency medicine providers prescribing less than fifteen or more than thirty prescriptions per day may be identified as outliers. In some embodiments, an outlier may be detected based on a combination of metrics falling outside of defined criteria (e.g., multiple metrics falling outside of their respective defined range of values).

Anomaly engine 130 may set various thresholds for different metrics. In some embodiments, anomaly engine 130 may use the reverse linear regression process described above to remove patient illness severity from each metric, and then set the threshold based on the normalized metric. For example, once the data is normalized for patient illness severity, an average length of stay may be defined to be between three and five days. A pediatrician with an average length of stay of six days therefore may be flagged as an outlier. As another example, it may be determined that an emergency medicine physician should not administer more than ten opioid prescriptions in a day. Prescribing more than ten opioid prescriptions may indicate, for example, that a certain provider is prescribing too many opioids and attracting certain patient populations to their practice. Thus, a physician prescribing more than ten opioid prescriptions per day may be determined to be an outlier.

Anomaly engine 130 may determine upper and lower threshold limits after normalizing the metrics (e.g., removing patient illness severity). For example, anomaly engine 130 may determine upper and lower threshold limits by calculating a standard deviation. Once a metric is normalized, the average of that metric value across a defined group (e.g., practice group, hospital, or specialty) may be calculated. Next, a standard deviation may be calculated from the average of the normalized metric values. Upper and lower threshold limits may be defined by adding a multiple of the standard deviation to the average normalized metric value. For example, upper and lower metric values may be set at one standard deviation from the average normalized metric value. Thus, any metric value greater than the upper limit, or less than the lower limit may be flagged as outliers. In addition or as an alternative to standard deviation, anomaly engine 130 may use any statistical dispersion method (e.g., range-based anomaly detection method) to determine upper and lower threshold limits, such as interquartile range (IQR) or other range calculation. By eliminating the impact of patient illness severity, providers can be fairly compared to identify true outliers. In turn, corrective action may be taken to improve medical care, identifying deviations from standard medical practices (e.g., overprescribing) and adjusting those practices to conform to normal limits.

Anomaly engine 130 may further update the threshold after determining the threshold is less than a degradation value. For example, if the threshold is approaching, equal to, or less than 0, anomaly engine 130 may use a degradation factor to increase the threshold. In some embodiments, the threshold may be a single value and anomaly engine may increase the single threshold value by the degradation factor. In some embodiments, the threshold may include an upper and lower limit. Here, anomaly engine 130 may increase both the upper and lower limit by the degradation factor. In some embodiments, anomaly engine 130 may increase the lower limit by the degradation factor and not change the upper limit. In some embodiments, anomaly engine 130 may increase the upper limit by the degradation factor but not the lower limit. Increasing the threshold by the degradation factor ensures that accurate outlier metrics may be detected.

In certain embodiments, anomaly engine 130 may ignore or disregard outliers if there is the sample size of data for comparison is small. Therefore, anomaly engine 130 may generate alerts only for metrics with a certain minimum number of occurrences. This may apply at the provider level, specialty level, or provider system (e.g., hospital, private practice, hospital system) level. For example, anomaly engine 130 may require a provider may have to have a certain number of treatments or claims before they may be evaluated for outlier detection. Similarly, a specialty group may need a certain number of treatments or claims before providers within the group are compared, or the group as a whole, is compared to other groups. Anomaly engine 130 may assign a threshold number of occurrences to each metric. In some embodiments, user computing device 110 may update the threshold number of occurrences associated with each metric.

Anomaly engine 130 may further be configured to detect and disregard false positives. A false positive may be a metric that appears to be an outlier, but in fact, is not. False positives may be associated with events or metrics that occur infrequently, such as mortality. Anomaly engine 130 may maintain an internal database of metrics likely to generate false positives. Anomaly engine 130 may ignore outliers from metrics on the false positive list. Anomaly engine 130 may set a higher threshold for these metrics in order to generate a false positive. For example, an outlier threshold for mortality may be set to two patients per day. In some embodiments, user computing device 110 may update the false positive list. In some embodiments, user computing device 110 may be configured to override anomaly engine's 130 determination that an outlier is a false positive.

As noted above, in some embodiments, anomaly engine 130 may be configured to assign upper and lower limits to each metric. The upper and lower limits may be unique to each provider. For example, each physician within a specialty group may have their own upper and lower limits for each metric. This may be a result of the level of sickness that provider typically treats. For example, a provider that treats sicker or more at-risk patients, may be assigned higher threshold limits for outlier detection than a physician treating patients with less severe illnesses.

In some embodiments, anomaly engine 130 may use artificial intelligence or machine learning to make certain inferences. For example, anomaly engine 130 may include a machine learning model trained to detect outliers. The machine learning model may use data at local store 132 as a training data set. Anomaly engine 130 may maintain a separate machine learning model for each data provider system 140. This may be desirable because each data provider system 140 may have different tolerances and metrics. Therefore, it may be desirable to use separate machine learning models for each data provider system 140 so that more precise patterns may be detected. The machine learning model may be configured to detect trends and anomalies within metrics. Additionally, the machine learning model may generate alerts when metrics pass or approach certain threshold values. This may be beneficial to provide automatic alerts to users within environment 100.

Anomaly engine 130 may train a machine learning model by iterating over received data and outputting whether the data includes an outlier. In some embodiments, the data used to train the machine learning model may or may not be normalized. The machine learning model may be further configured to output metrics or data categories that likely include outliers based on the current data or metric. For instance, an example may include a number of surgery complications and a label that the value is an outlier. The machine learning model may be trained to associate other metrics that are likely outliers, based on this one. For example, surgery complications may be associated with increased average length of stay in a hospital. Therefore, machine learning model may also output that the average length of stay associated with the provider is an outlier. Leveraging machine learning may be useful to draw additional inferences between data values to detect outliers. Such an architecture enhances real-time detection of outliers and allow faster decisions to be made regarding providers, their privileges, and methods of treatment.

In some embodiments, anomaly engine 130 may be configured to host an interface that may be accessed via network 120. For example, user computing device 110 may use the interface to interact with anomaly engine 130. Anomaly engine 130 may be further configured to send notifications or alerts. Notifications may be sent as SMS messages, emails, and/or phone calls. In some embodiments, notifications may be sent to an application (e.g., user application 116) installed on user computing device 110 that provides access to anomaly engine 130. The notification may include a link that, when interacted with, launches a GUI providing an interface to anomaly engine 130. In some embodiments, anomaly engine 130 may transmit a notification to user computing device 110 if an outlier is detected. The alert may launch user application 116 causing display device 114 to show the outlier. Anomaly engine 130 may be further configured to interface with medical device 150.

Medical device 150 may be any device or apparatus in a healthcare environment. For example, medical device 150 may be used to house medication. As another example, medical device 150 may be a surgical implement. In some embodiments, medical device 150 may be located at data provider system 140. For example, if data provider system 140 is a hospital, medical device 150 may be a medicine storage device within the hospital. In some embodiments, medical device 150 may be located separate from data provider system 140. For example, data provider system 140 may be a data center affiliated with a hospital, and medical device 150 may be located at the hospital.

Access device 152 may be used to govern access to medical device 150. In some embodiments, access device 152 may be a lock that is opened by a key. Access device 152 may use radio frequency identification (RFID) to determine access. Access device 152 may receive an access request and determine whether the requestor has the necessary permissions to use medical device 150. For example, a pharmacist may need medication stored at medical device 150 to fill a prescription. The pharmacist may first swipe a keycard at access device 152 in order to gain access to medical device 150. Access device 152 may determine whether the pharmacist has permission to access medical device 150. Access device 152 may determine the permission by communicating with medical device 150 and/or data provider system 140. If access device 152 determines the pharmacist has requisite permissions, access device 152 provides access to medical device 150. For example, access device 152 may disengage a lock at medical device 150.

Medical device 150 may communicate with other entities on network 120 via communication interface 112-4. For example, medical device 150 may receive a message from user computing device 110 to alter permissions for a provider at access device 152. The message may be based on an outlier detected by anomaly engine 130. In some embodiments, anomaly engine 130 may automatically send a message to medical device 150 to alter permissions based on outlier detection. For example, anomaly engine 130 may detect that physician within the pediatric department is an outlier with respect to the rate of opioids prescribed. In response, anomaly engine 130 may automatically transmit a message to medical device 150, restricting the physician's access. The permission change may apply to multiple medical devices 150. For example, a hospital may house fifty medicine storage cabinets (e.g., medical devices 150). The updated permission may apply to all fifty medicine storage cabinets, or a subset thereof.

Figure 2A:
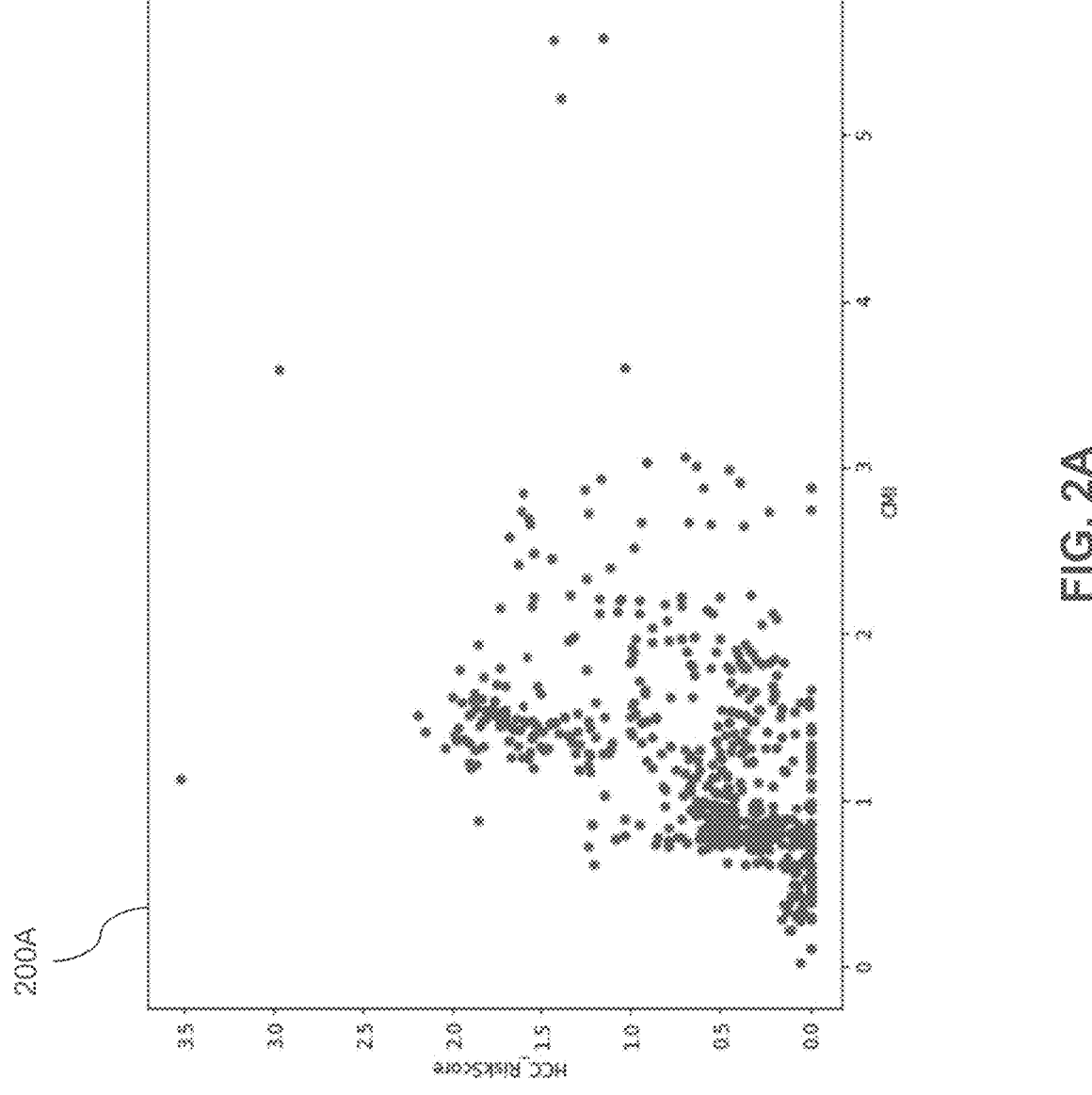
FIG. 2A depicts an example plot of metric values, according to some embodiments.

FIG. 2A depicts an example plot 200A of metric values, according to some embodiments. Plot 200A includes a plot of case mix index (CMI) and hierarchical condition category (HCC) response. Case mix index may be used to categorize or determine the amount of reimbursement a hospital (e.g., data provider system 140) may receive. HCC may be a risk score assigned to a patient based on their current illnesses.

Anomaly engine 130 may determine an HCC for a physician based on claim data. In some embodiments, anomaly engine 130 may receive an HCC score. As depicted in plot 200A, physicians with higher HCC scores (e.g., physicians that treat patients with more severe illnesses) also have higher CMI scores. Plot 200A thus illustrates the impact of patient illness severity on comparison metrics (e.g., CMI). Therefore, it may not be accurate to compare the CMI scores of two physicians for purposes of outlier detection.

Figure 2B:
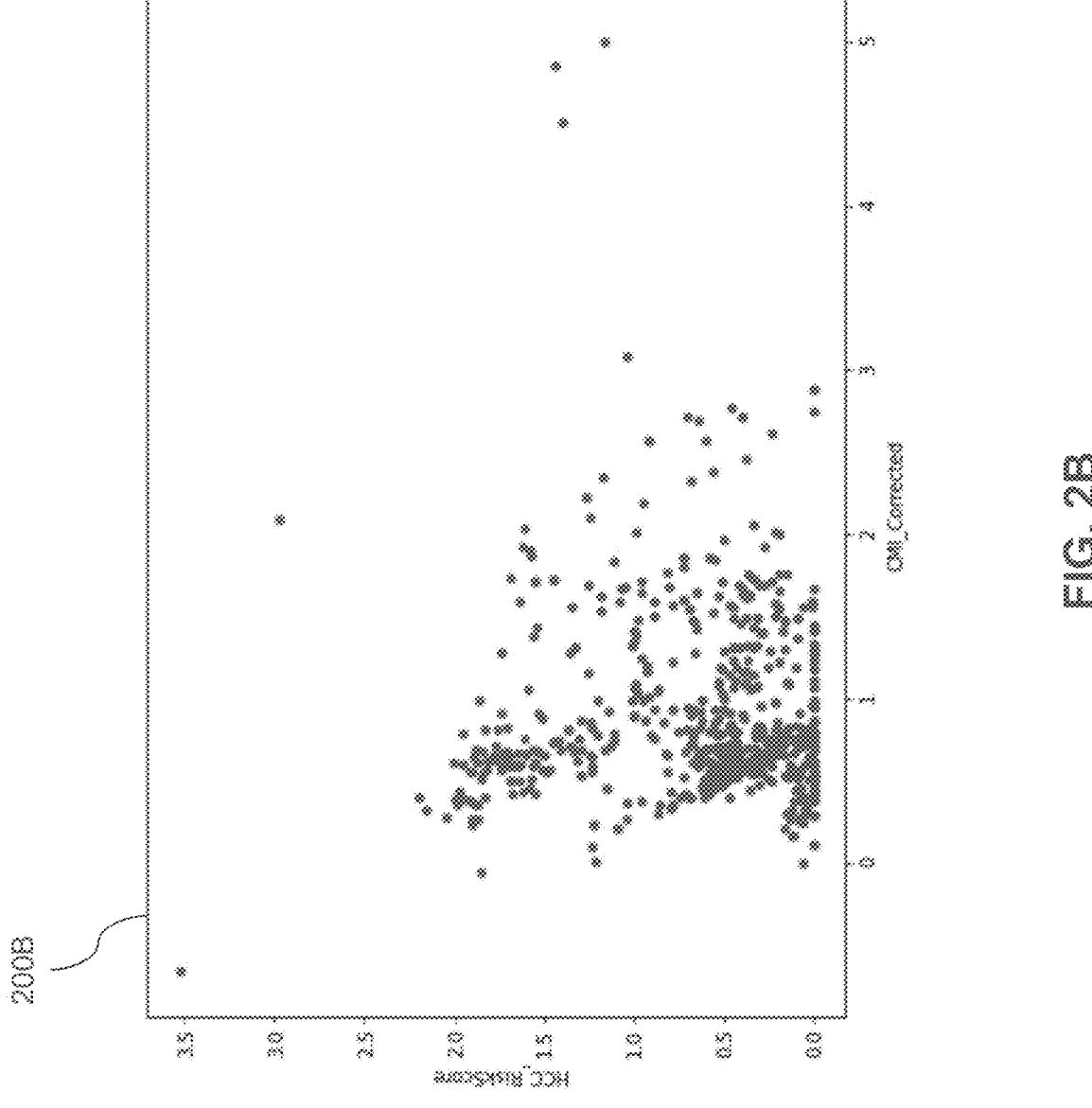
FIG. 2B depicts an example plot of normalized metric values, according to some embodiments.

FIG. 2B depicts an example plot 200B of normalized metric values, according to some embodiments. Plot 200B also depicts CMI and HCC, with the HCC values normalized based on severity of patient illness. Once the HCC values are normalized, and the patient illness severity risk is eliminated, the CMI values may be compared to detect outliers. Although plots 200A and 200B depict HCC and CMI, any metrics may be illustrated for these purposes. For example, HCC and average length of stay (ALOS) may be compared, or HCC and amount of medication prescribed.

Figure 3A:
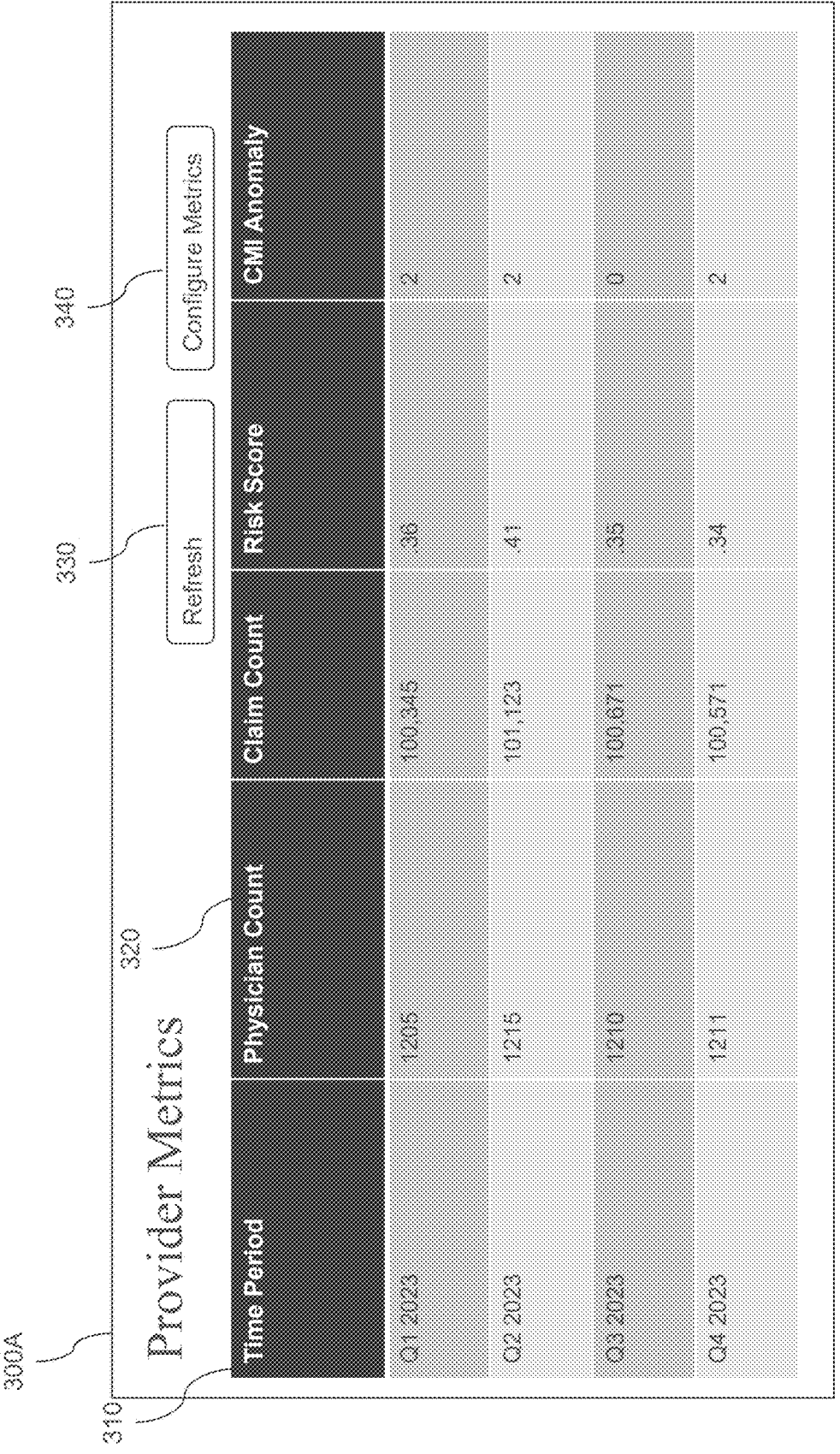
FIG. 3A depicts an exemplary interface for displaying current metrics, according to some embodiments.

FIG. 3A depicts an exemplary interface 300A for displaying current metrics, according to some embodiments. User computing device 110 may access interface 300A when it connects to anomaly engine 130 via user application 116. Interface 300A includes time period 310, metrics 320, refresh 330, and configure metrics 340. Time period 310 may be a field allowing a user to organize metrics 320 by time. Time period 310 may be updated by user computing device 110 or anomaly engine 130. Time period 310 may be defined quarterly, monthly, weekly, etc. Metrics 320 may be values designated for display at interface 300A. Metrics 320 may be configured by user computing device 110 and anomaly engine 130. For example, user computing device 110 may designate which metrics 320 are retrieved from data provider system 140 and displayed at interface 300A. For example, metrics 320 may include physician count, claim count, risk score, and CMI anomaly. Interface 300A may include other metrics 320 such as average length of stay (ALOS) anomaly, denial rate, readmission rate, prescription rate, audit rate, and/or mortality rate. Refresh 330 may be a button configured to update the metrics displayed at interface 300A. For example, when a user at user computing device 110 selects refresh 330, anomaly engine 130 may query data provider system 140 for updated metric values. Configure metrics 340 may be a button configured to allow user computing device 110 to edit metrics 320. For example, user computing device 110 may wish to add or delete metrics 320 at interface 300A. Configure metrics 340 may be used to remove metrics 320 currently displayed. Configure metrics 340 may further allow metrics 320 to be added. Metrics 320 that are added may be retrieved from data provider system 140.

Figure 3B:
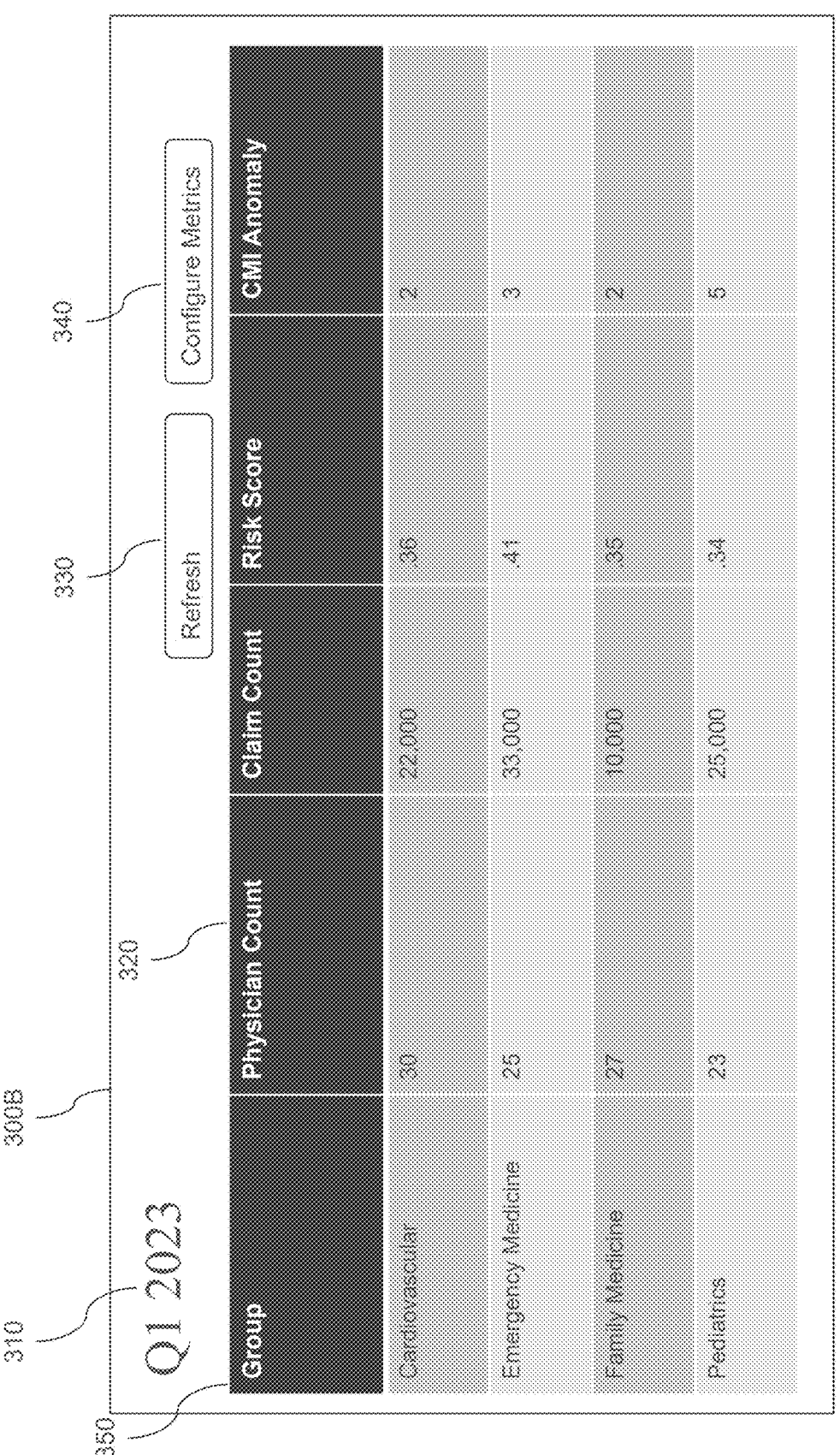
FIG. 3B depicts an exemplary interface for displaying current metrics, according to some embodiments.

FIG. 3B depicts an exemplary interface 300B for displaying current metrics, according to some embodiments. User computing device 110 may access interface 300B when it connects to anomaly engine 130 via user application 116. Interface 300B may be shown, for example, when time period 310 is selected in interface 300A. Interface 300B includes metrics 320 for a selected time period 310. For example, interface 300B may include metrics 320 over Q1 of 2023. As discussed above, time period 310 may be updated to any time range by user computing device 110 and/or anomaly engine 130. Interface 300B may include metrics 320 for one or more groups 350. Each group 350 may correspond to a physician specialty group. For example, group 350 may be cardiovascular, emergency medicine, family medicine, or pediatrics. Each group may include a provider assigned by anomaly engine 130. User computing device 110 and/or anomaly engine 130 may be configured to define additional groups 350. Each metric 320 may be updated to show values associated with each group 350. For example, physician count may be updated to show values for cardiovascular group 350-1 and emergency medicine group 340-2.

Figure 3C:
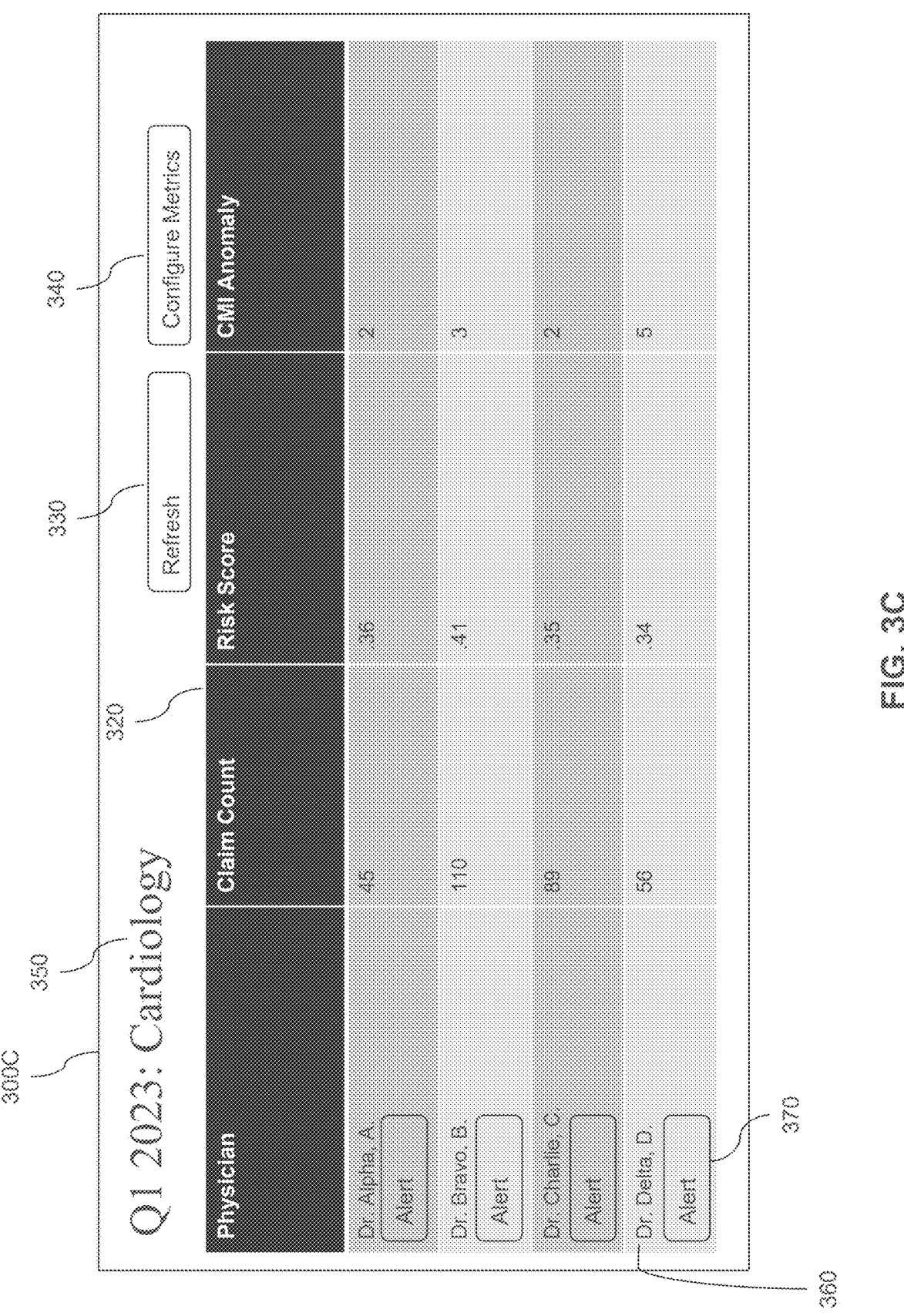
FIG. 3C depicts an exemplary interface for displaying current metrics, according to some embodiments.

FIG. 3C depicts an exemplary interface 300C for displaying current metrics, according to some embodiments. Interface 300C may show metrics 320 for group 350. Interface 300C may be configured to display provider 360 and alert 370. Provider 360 may be an individual assigned to group 350. For example, if group 350 corresponds to cardiology, interface 300C may display each provider 360 assigned to cardiology group 350. Alert 370 may be a button configured to generate an alert that is sent to provider 360. The alert may include metrics 320 shown at interface 300C. In some embodiments, when alert 360 is clicked, any metric 320 anomaly engine 130 has access to may be included in the alert. In some embodiments, the data may already be at anomaly engine 130. In some embodiments, the selected metric 320 may not be at anomaly engine 130. In this example, anomaly engine 130 may retrieve the data from data provider system 140 in order to include it within the alert.

Figure 4:
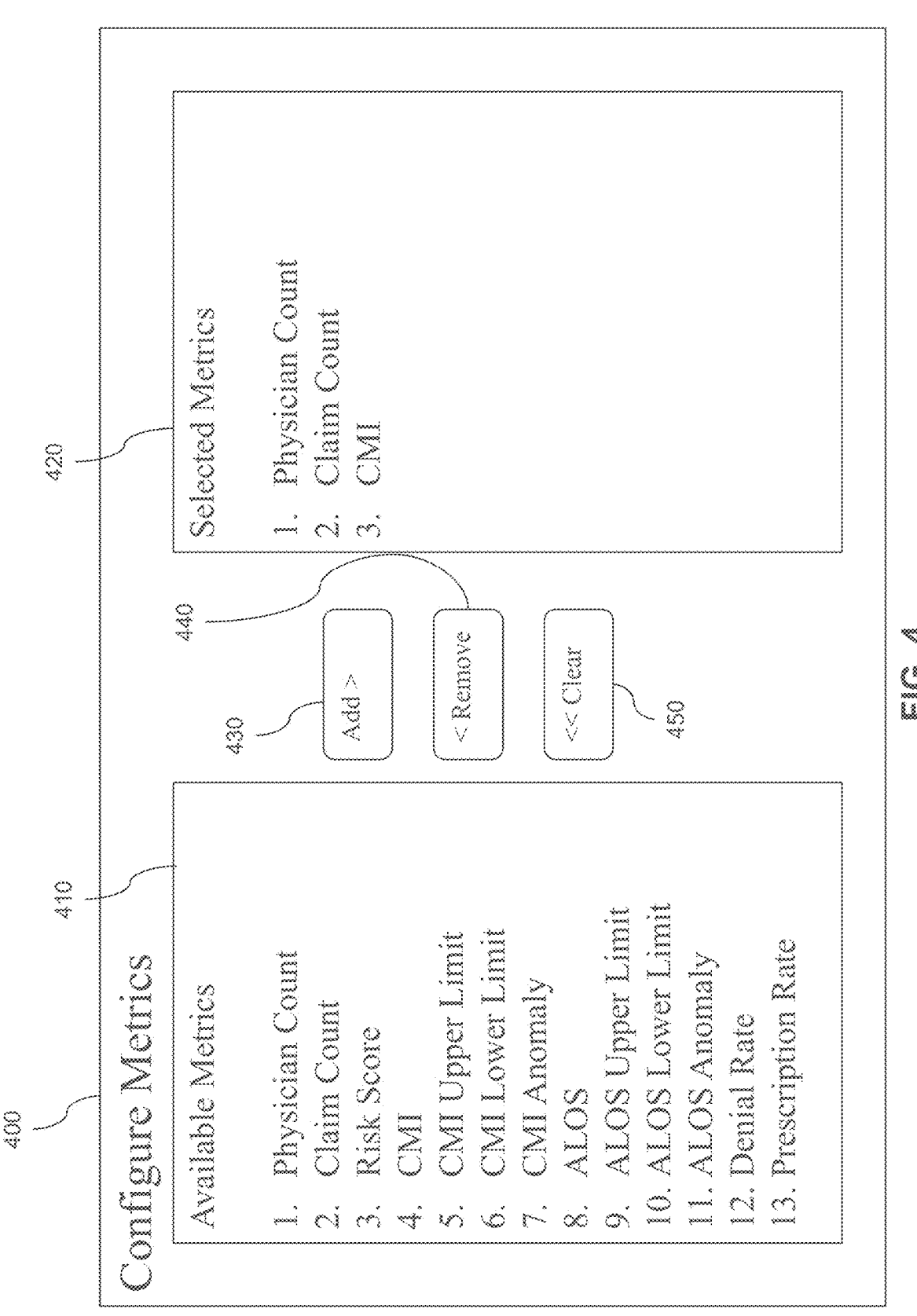
FIG. 4 depicts an exemplary interface for configuring an anomaly engine, according to some embodiments.

FIG. 4 depicts an exemplary interface 400 for configuring anomaly engine 130, according to some embodiments. Interface 400 includes available metrics 410, selected metrics 420, add metric 430, remove metric 440, and clear metrics 450. Interface 400 may be displayed on user computing device 110, for example, when configure metrics 340 is selected. Available metrics 410 may display metrics 320 that are available from data provider system 140. Available metrics 410 may not all be stored at anomaly engine 130. For example, anomaly engine 130 may only retrieve selected metrics 420 out of those available at data provider system 140. In some embodiments, anomaly engine 130 may automatically retrieve certain metrics based on the output of a machine learning model. For example, a machine learning model at anomaly engine 130 may determine that two metrics are highly correlated. In this instance, when one metric is part of selected metrics 420, anomaly engine 130 may automatically retrieve the other correlated metrics for analysis. This is beneficial to identify additional outlier data and provide real-time analysis.

Selected metrics 420 may list metrics 320 that have been selected to show at interface 300 (e.g., interface 300A, 300B, and/or 300C). Add metrics 430 may be used to add metrics 420 to track and show at interface 300 (e.g., interface 300A, 300B, and/or 300C). For example, entries at available metrics 410 may be highlighted and then added to selected metrics 420 by clicking add metrics 430. Remove metrics 440 may remove selected metrics 420. Once removed, anomaly engine 130 may stop retrieving metric 320 from data provider system 140. Clear metrics 450 may remove all selected metrics 420.

Figure 5A:
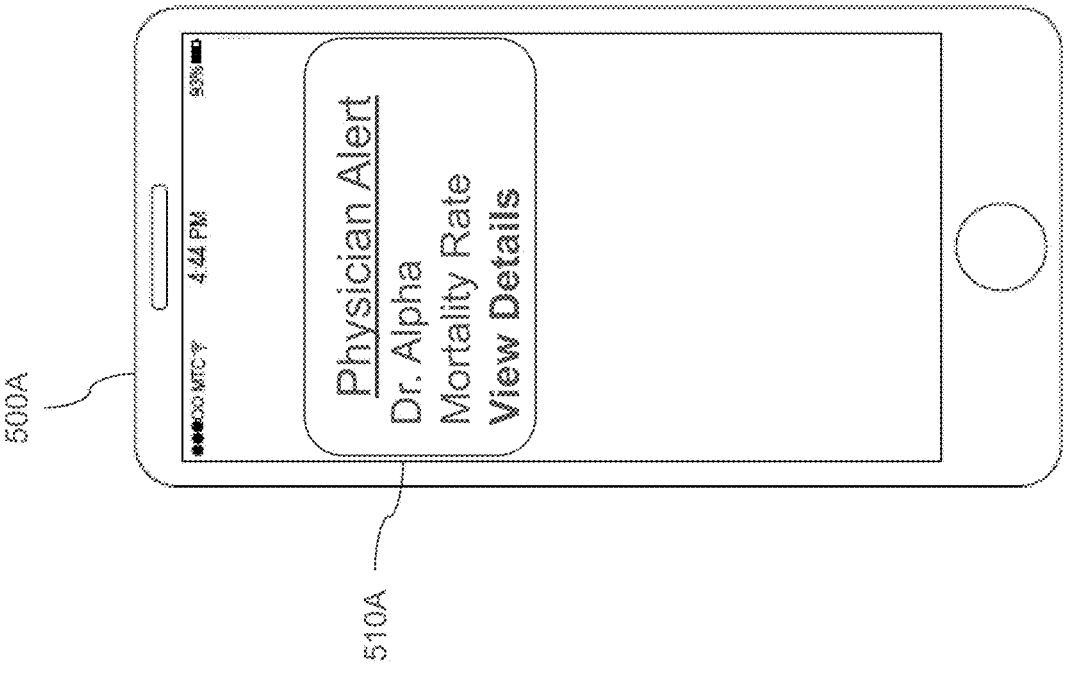
FIG. 5A depicts an exemplary interface for receiving and displaying an alert, according to some embodiments.

FIG. 5A depicts an exemplary interface 500A for receiving and displaying an alert, according to some embodiments. Interface 500A may display alert 510A on user computing device 110 when an alert is received. The alert may be generated automatically by anomaly engine 130 as a result of identifying an outlier. As discussed above, alerts may be generated when metrics pass predefined threshold values. Such alerts provide real-time warnings regarding certain physician actions. For example, the amount of certain medications prescribed may be tracked in real time. This may be desirable to understand physician prescribing patterns, but also to identify potential illicit behavior by the physician.

Additionally, it may be desirable to protect patients from having been prescribed too much medication. In addition to the alert, in some embodiments, anomaly engine 130 may also send a message to medical device 150, altering permissions associated with the provider listed in the alert.

Figure 5B:
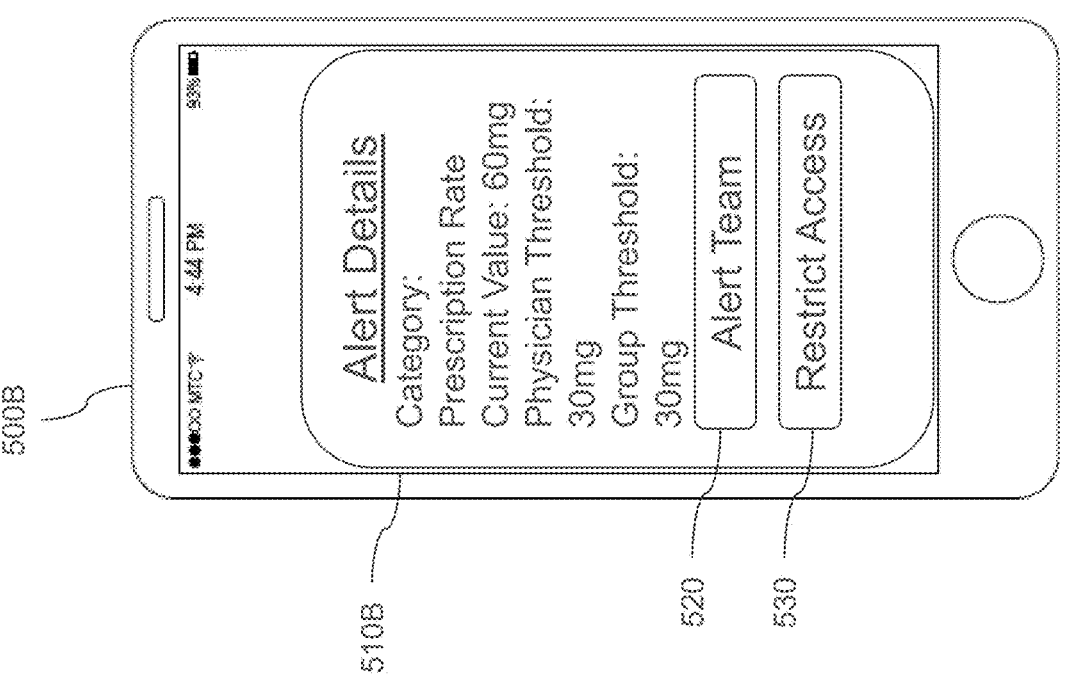
FIG. 5B depicts an exemplary interface for receiving and displaying an alert, according to some embodiments.

FIG. 5B depicts an exemplary interface 500B for an alert, according to some embodiments. Interface 500B may display alert 510B on user computing device 110. Interface 500B may be shown when a user interacts with alert 510A. Alert 510B may display additional information regarding the received alert. For example, alert 510B may display the metric to which the alert is linked, the current value of the metric, the metric threshold assigned to the physician, and the metric threshold for the physician's specialty group.

Interface 500B includes alert team 520 and restrict access 530. Alert team 520 may be configured to directly forward the alert to user computing devices 110 linked to the provider identified within the alert. For example, the provider may be part of a team, and each team member may receive the alert when alert team 520 is pressed. Alert team 520 may cause user computing devices 110 of the linked team members to display the alert. In some embodiments, the alert may cause user computing device 110 to vibrate and/or make a noise.

Restrict access 530 may be configured to change the provider's privileges, in real time, so as to prevent or mitigate any harm inferred from the metric. For example, a physician in a hospital may have privileges to prescribe any medication. Anomaly engine 130 may detect that the physician has prescribed an amount of opioids greater than a predefined amount in a given time period. This may cause an alert to be sent and received by user computing device 110. In some embodiments, the alert may be alert 510B on interface 500B. In response, user computing device 110 may select restrict access 530. This may send a message to data provider system 140 and update the provider's permission levels. For example, the provider may no longer be able to prescribe the medication related to the alert, or any medication, as a result. In some embodiments, access device 152 may no longer permit the provider to access or utilize medical device 150. This may be beneficial to rapidly detect and quarantine any detected anomalies within the healthcare environment. Additionally, it will allow other providers or administrative personnel to review the metric and determine whether the alert was generated by accident.

Restrict access 530 may also be useful in scenarios where anomaly engine 130 does not automatically update a provider's permissions. For example, anomaly engine 130 may be configured to change permissions based on certain metrics (e.g., opioids prescribed, surgical errors) or metric variations. For instance, an alert may be generated if the difference between the two latest metric values varies by a predefined amount. In some embodiments, an alert may be triggered if a metric value differs from a threshold by a predefined amount. In some embodiments, anomaly engine 130 may only generate an alert in response to an outlier, without causing a change to permissions. In this instance, a user may still restrict the provider's access via restrict access 530.

FIG. 6 is a flowchart illustrating an example process 600 for detecting and displaying healthcare outlier data, according to some embodiments. Process 600 may be performed by processing logic that may comprise hardware (e.g., circuitry, dedicated logic, programmable logic, microcode, etc.), software (e.g., instructions executing on a processing device), or a combination thereof. One or more of the steps in FIG. 6 may be performed by anomaly engine 130. In some embodiments, one or more of the steps shown in FIG. 6 may be omitted, repeated, and/or performed in a different order than the order shown in FIG. 6. Accordingly, the scope of the invention should not be considered limited to the specific arrangement of steps shown in FIG. 6. The steps shown in FIG. 6 may be implemented as computer-readable instructions stored on computer-readable media, where, when the instructions are executed, cause a processor to perform the process of FIG. 6.

At 610, anomaly engine 130 receives a claim that includes a provider, an illness, a treatment, and a risk score based on the illness and the treatment. The claim may be sent by data provider system 140. In some embodiments, data provider system 140 may automatically send the claim. In some embodiments, anomaly engine 130 may request claims it has not yet received. In some embodiments, anomaly engine 130 may compute or update the risk score. For example, anomaly engine 130 may determine a patient risk score based on the patient's medical history, their current illness, and treatment. The claim may be received via network 120.

At 620, anomaly engine 130 updates a metric (e.g., a statistic) associated with the provider and/or data provider system 140 (e.g., a hospital) based on the claim. In some embodiments, anomaly engine 130 may use the illness, treatment, and risk score to update the metric. The metric may be any statistic or other data that anomaly engine 130 tracks. For example, the metric may be, without limitation, mortality rate, length of stay, readmission rate, audit rate, average total charges value, denial rate, medicine prescription rate, illness, treatment, and treatment cost. For example, the claim may state that the patient stayed at the hospital for five nights, which may be used to update an average length of stay metric associated with the provider.

In some embodiments, the metric being updated may be stored at local store 132. In some embodiments, anomaly engine 130 may retrieve a metric from data provider system 140, update it using the claim, and store the updated metric value at local store 132.

In some embodiments, anomaly engine 130 may request additional metrics from data provider system 140. For example, the claim may have been submitted by a cardiologist at a hospital (e.g., data provider system 140). In order to determine whether the treatment indicated in the claim may be an outlier, anomaly engine 130 may request metrics associated with other cardiologists from the same hospital. As another example, anomaly engine 130 may request all data stored by data provider system 140 regarding the patient identified in the claim. This may be beneficial so that anomaly engine 130 may compute a patient risk score for normalization purposes.

At 630, anomaly engine 130 normalizes the metric using the risk score, the illness, and the treatment. The normalization may involve updating the metric to reduce the effect of patient illness severity on the metric. The patient illness severity may be represented by the risk score. Anomaly engine 130 may use the reverse linear regression process described above with respect to FIG. 1 to normalize the metric. The result of the normalization may be that the same metric between two providers who treat different patients may be fairly compared. This normalization is critical to accurately determining when providers are operating outside normal limits. For example, a provider prescribing too much medication may have their access privileges suspended or revoked. In some embodiments, anomaly engine 130 may normalize all metrics related to the claim, or a subset thereof.

At 640, anomaly engine 130 determines the normalized metric is an outlier by comparing the normalized metric to a threshold. In some embodiments, the threshold may take the form of a single value, or the threshold may include a lower limit and an upper limit. The threshold may be defined such that a normalized metric lower than the lower limit or greater than the upper limit may be considered an outlier. In some embodiments, prior to comparing the normalized metric to the threshold, the normalized metric value may be used to update the threshold. For example, the threshold may be updated based on the difference between the metric and the normalized metric. In some embodiments where the threshold includes an upper limit and a lower limit, the limits may be set based on a variance from the normalized metric value, such as one standard deviation above and below the normalized metric value. Adjusting the threshold for each metric is beneficial so that a comparison of the normalized metric to the threshold accurately indicates whether the metric is an outlier.

In some embodiments, anomaly engine 130 may make further adjustments to the threshold so that outliers may accurately be detected. For example, the adjusted threshold (e.g., single value, upper and lower limit) may be less than a degradation value. For example, a degradation value may be 0.1. In this instance, anomaly engine 130 may increase the threshold (e.g., single value, upper and lower limit) so that an outlier is detected. Anomaly engine 130 may increase the threshold by a degradation factor such as 0.5, so that the new threshold is at least 0.6. This may be beneficial so that false positive outliers are not mistakenly detected by having a threshold value that is too low (e.g., approaching zero).

In some embodiments, anomaly engine 130 may further determine whether the normalized metric is associated with a statistically significant number of claims. The statistically significant number of claims may be any predefined value. Using a statistically significant number of claims is beneficial to ensure that a true metric outlier is identified. If the sample size is too small, anomaly engine 130 may determine that the metric does not yet indicate an outlier. For example, a new provider may not have treated any patients. Thus, once the providers treats a first patient, it may be inaccurate to label any metrics associated with the first treatment as an outlier. Therefore, anomaly engine 130 may require a statistically significant number of claims, such as 100, 1,000, or 10,000, before determining a metric associated with the provider is an outlier.

In some embodiments, anomaly engine 130 may further determine whether the metric is a false positive. A false positive may be a metric that appears to be an outlier, but is not. This determination may be based on the rarity of the event. For example, a private practice may experience one mortality every six months. However, if the private practice experiences a second mortality during a six month window this may not necessarily indicate it is an outlier. Here, it may be labeled as a false positive and thus not determined to be an outlier.

At 650, if the normalized metric is determined to be an outlier, anomaly engine 130 presents an indication of the outlier to a user. In some embodiments, local store 132 may store information associating users to particular metrics. Thus, when an outlier is detected for a particular metric, the outlier may be presented to users associated with that metric (e.g., users interested in being informed when an outlier is detected). In some embodiments, anomaly engine 130 sends an alert to a user computing device associated with the user, such as user computing device 110, which may be displayed at the computing device upon receipt. In some embodiments, the alert may be configured to cause a display at the user computing device to display the alert. For example, when received, the alert may activate display device 114 at user computing device 110. This may be beneficial so that a user associated with user computing device 110 can immediately view and react to the alert. In some embodiments, the alert may cause user computing device 110 to vibrate and/or generate a noise.

In some embodiments, the alert may include a provider identifier (e.g., name, employee ID), the metric, the metric value, and the threshold. In some embodiments, the alert may include historical values for the metric. The historical values may be shown over a time period. For example, the historical values may be shown for the last week, last month, or last year.

The alert may further include a link to access a graphical user interface (GUI). The GUI may include the normalized metric, the provider, the claim, and the risk score. The GUI may further include a button to alert a team associated with the provider. For example, when pressed, user computing device 110 may forward the alert to other user computing devices 110 associated with the provider. For example, the provider may be part of a cardiology specialty group, and the alert team button may forward the alert to other members of the cardiology specialty group. The GUI may further include a restrict access button. The restrict access button may send a communication over network 120 to anomaly engine 130, data provider system, and/or medical device 150 to update permissions associated with the provider and the metric. User computing device 110 may access the GUI over network 120.

At 660, anomaly engine 130 updates a permission associated with a medical device, such as medical device 150. In some embodiments, the updated permission is configured to prevent access by the provider. The updated permission may be based on the determined outlier metric. In some embodiments, anomaly engine 130 may automatically update the permission. For example, if the outlier metric is rate of opioids prescribed, anomaly engine 130 may update the provider's permissions to lock them out of a medicine cabinet (e.g., medical device 150) at their hospital (e.g., data provider system 140). In some embodiments, anomaly engine 130 may update the permission based on an input from user computing device 110. For example, a user at user computing device 110 may interact with the alert in order to update the permissions. The permission may be associated with devices linked to the metric. For example, if the metric is an amount of opioids prescribed per day, the permission may revoke the ability to prescribe additional opioids. The permission may be updated at all computers, devices, or other electronic means that allow the provider prescribe opioids.

Figure 7:
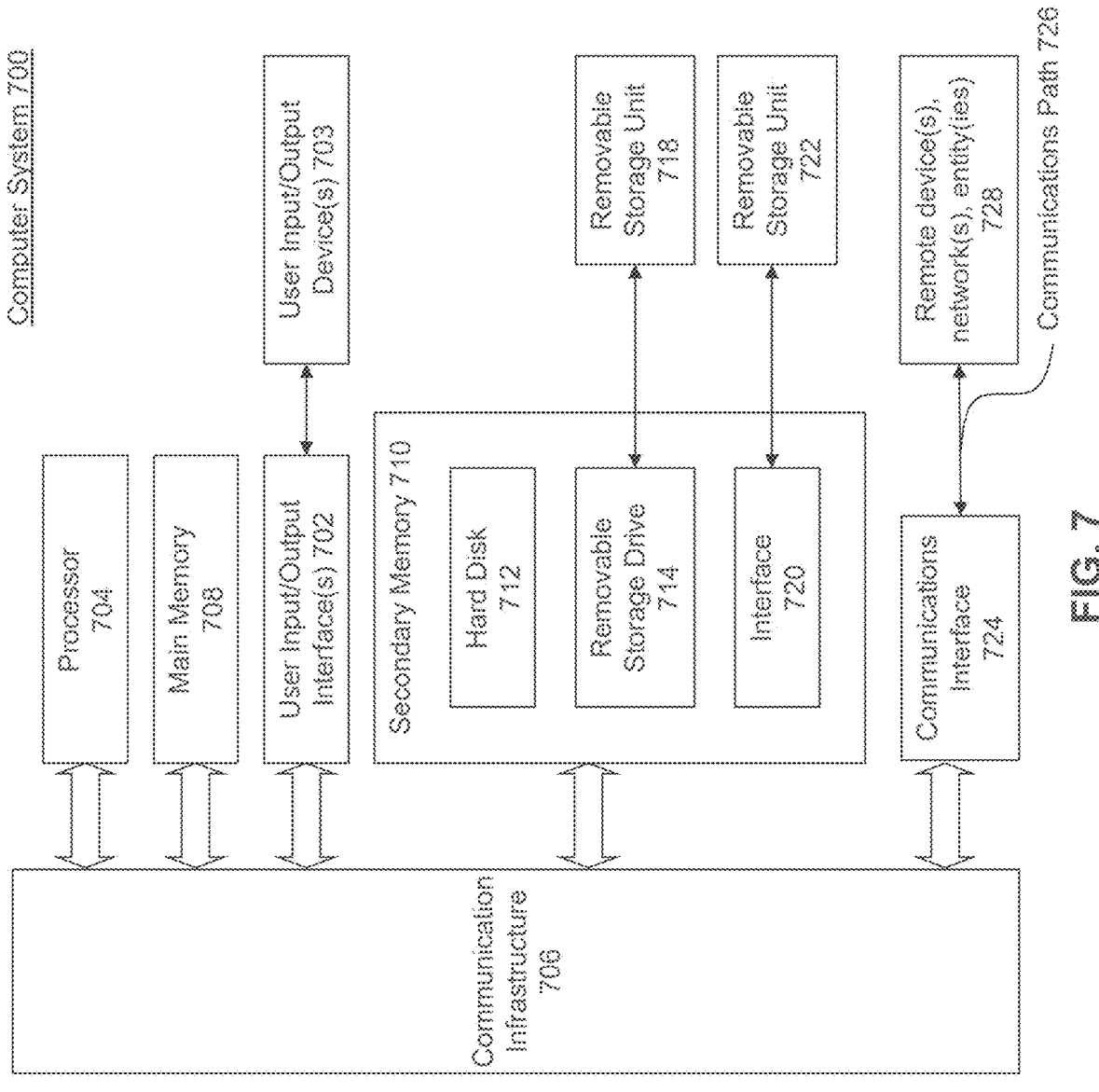
FIG. 7 depicts an example computer system useful for implementing various embodiments.

Various embodiments may be implemented, for example, using one or more well-known computer systems, such as computer system 700 shown in FIG. 7. One or more computer systems 700 may be used, for example, to implement any of the embodiments discussed herein, as well as combinations and sub-combinations thereof.

Computer system 700 may include one or more processors (also called central processing units, or CPUs), such as a processor 704. Processor 704 may be connected to a communication infrastructure or bus 706.

Computer system 700 may also include user input/output device(s) 703, such as monitors, keyboards, pointing devices, etc., which may communicate with communication infrastructure 706 through user input/output interface(s) 702.

One or more of processors 704 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 700 may also include a main or primary memory 708, such as random access memory (RAM). Main memory 708 may include one or more levels of cache. Main memory 708 may have stored therein control logic (i.e., computer software) and/or data.

Computer system 700 may also include one or more secondary storage devices or memory 710. Secondary memory 710 may include, for example, a hard disk drive 712 and/or a removable storage device or drive 714. Removable storage drive 714 may be a floppy disk drive, a magnetic tape drive, a compact disk drive, an optical storage device, tape backup device, and/or any other storage device/drive.

Removable storage drive 714 may interact with a removable storage unit 718. Removable storage unit 718 may include a computer usable or readable storage device having stored thereon computer software (control logic) and/or data. Removable storage unit 718 may be a floppy disk, magnetic tape, compact disk, DVD, optical storage disk, and/any other computer data storage device. Removable storage drive 714 may read from and/or write to removable storage unit 718.

Secondary memory 710 may include other means, devices, components, instrumentalities or other approaches for allowing computer programs and/or other instructions and/or data to be accessed by computer system 700. Such means, devices, components, instrumentalities or other approaches may include, for example, a removable storage unit 722 and an interface 720. Examples of the removable storage unit 722 and the interface 720 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 700 may further include a communication or network interface 724. Communication interface 724 may enable computer system 700 to communicate and interact with any combination of external devices, external networks, external entities, etc. (individually and collectively referenced by reference number 728). For example, communication interface 724 may allow computer system 700 to communicate with external or remote devices 728 over communications path 726, which may be wired and/or wireless (or a combination thereof), and which may include any combination of LANs, WANs, the Internet, etc. Control logic and/or data may be transmitted to and from computer system 700 via communication path 726.

Computer system 700 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 700 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 700 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 700, main memory 708, secondary memory 710, and removable storage units 718 and 722, as well as tangible articles of manufacture embodying any combination of the foregoing. Such control logic, when executed by one or more data processing devices (such as computer system 700), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 7. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer-implemented method, comprising:
receiving, by one or more computing devices, a first claim including a provider, an illness, a treatment, a code, and a risk score, wherein the risk score is based on the illness and the treatment;
in real-time in response to receiving the first claim:
grouping, by the one or more computing devices, based on the code, the provider into a specialty group;
updating, by the one or more computing devices, a metric associated with the provider based on the first claim;
computing, by the one or more computing devices and based on historical risk score and metric data of the specialty group corresponding to a dynamic rolling time window, a risk impact coefficient, wherein the risk impact coefficient represents a linear relationship between the metric and the risk score;
determining, by the one or more computing devices, an impact of the risk score based on the risk impact coefficient and the risk score;
subtracting, by the one or more computing devices, the impact of the risk score from the metric to generate a normalized metric value;
determining, by the one or more computing devices, that the normalized metric value is an outlier by:
comparing, by the one or more computing devices, the normalized metric value to a threshold corresponding to the specialty group; and
determining, by the one or more computing devices and based on the specialty group, that the normalized metric value is associated with a statistically significant number of claims; and
in response to determining that the normalized metric value is an outlier,
transmitting, by the one or more computing devices, an alert to a client device associated with a user, wherein the alert is configured to cause a display of the client device to display an indication of the outlier.

2. The computer-implemented method of claim 1, wherein comparing the normalized metric value to the threshold comprises:

generating, by the one or more computing devices, a first quartile value and a second quartile value based on a plurality of normalized metric values corresponding to a plurality of providers of the specialty group;

determining, by the one or more computing devices, an interquartile range based on the first quartile value and the second quartile value;

calculating, by the one or more computing devices, a median value of the interquartile range;

calculating, by the one or more computing devices, a lower limit of the threshold based on the median value, a threshold multiplier, and the interquartile range;

calculating, by the one or more computing devices, an upper limit of the threshold based on the median value, the threshold multiplier, and the interquartile range; and determining, by the one or more computing devices, the normalized metric value is an outlier based on the normalized metric value being greater than the upper limit of the threshold or less than the lower limit of the threshold.

3. The method of claim 2, further comprising:

determining, by the one or more computing devices, one of the lower limit of the threshold or the upper limit of the threshold is less than a degradation value; and in response to the determining, increasing, by the one or more computing devices, one of the lower limit of the threshold or the upper limit of the threshold by a degradation factor.

4. The computer-implemented method of 1, further comprising:

updating, by the one or more computing devices, a permission associated with a medical device, wherein the updated permission is configured to prevent access by the provider.

5. The computer-implemented method of claim 1, wherein grouping the provider into the specialty group further comprises:

retrieving, by the one or more computing devices, the code from the first claim;

transmitting, by the one or more computing devices, a request for the specialty group to a data provider system, the request including the code and the provider;

receiving, by the one or more computing devices, the specialty group from the data provider system; and assigning, by the one or more computing devices, the provider to the specialty group.

6. The computer-implemented method of claim 1, wherein the alert includes a link to access a graphical user interface providing additional information associated with the alert.

7. The computer-implemented method of claim 1, wherein the metric is one of mortality rate, length of stay, readmission rate, audit rate, average total charges value, denial rate, or medicine prescription rate.

8. The computer-implemented method of claim 1, wherein determining that the normalized metric value is an outlier further comprises:

training a machine learning model on a plurality of previously received claims, wherein each claim of the plurality of previously received claims includes a respective first metric that is labeled as an outlier, and wherein the training comprises:

for each of the previously received claims, determining, by the machine learning model, a respective second metric correlated to the respective first metric of the previously received claim and labeling the respective second metric as an outlier; and retraining the machine learning model on the plurality of previously received claims with the labeled respective second metrics;

wherein the training configures the machine learning model to determine whether a third metric is an outlier based on a claim associated with the third metric;

inputting the first claim into the machine learning model; and determining, by the machine learning model, the normalized metric value associated with the provider is an outlier.

9. The computer-implemented method of claim 1, further comprising:

identifying, by the one or more computing devices, that the metric is included in an internal database; and based on identifying that the metric is included in the internal database:

determining, by the one or more computing devices, a plurality of contributing claims associated with the provider, wherein the plurality of contributing claims contributed to the metric associated with the provider and have non-zero metric values;

determining, by the one or more computing devices, that the outlier is a false positive based on a number of the plurality of contributing claims being less than or equal to a coincidence threshold; and in response to determining that the outlier is a false positive, suppressing, by the one or more computing devices, the alert.

10. The computer-implemented method of claim 1, wherein determining that the normalized metric value is associated with the statistically significant number of claims comprises:

determining, by the one or more computing devices, a number of eligible claims associated with the provider exceeds a minimum claims threshold.

11. A system, comprising:

a memory; and at least one processor coupled to the memory and configured to:

receive a first claim including a provider, an illness, a treatment, a code, and a risk score, wherein the risk score is based on the illness and the treatment;

in real-time in response to receiving the first claim:

group, based on the code, the provider into a specialty group;

update a metric associated with the provider based on the first claim;

compute, based on historical risk score and metric data of the specialty group corresponding to a dynamic rolling time window, a risk impact coefficient, wherein the risk impact coefficient represents a linear relationship between the metric and the risk score;

determine an impact of the risk score based on the risk impact coefficient and the risk score;

subtract the impact of the risk score from the metric to generate a normalized metric value;

determine that the normalized metric is an outlier, wherein the at least one processor is further configured to:

compare the normalized metric to a threshold corresponding to the specialty group; and determine, based on the specialty group, that the normalized metric is associated with a statistically significant number of claims; and in response to determining that the normalized metric is an outlier, transmit an alert to a client device associated with a user, wherein the alert is configured to cause a display of the client device to display an indication of the outlier.

12. The system of claim 11, wherein to compare the normalized metric value to the threshold, the at least one processor is further configured to:

generate a first quartile value and a second quartile value based on a plurality of normalized metric values corresponding to a plurality of providers of the specialty group;

determine an interquartile range based on the first quartile value and the second quartile value;

calculate a median value of the interquartile range;

calculate a lower limit of the threshold based on the median value, a threshold multiplier, and the interquartile range;

calculate an upper limit of the threshold based on the median value, the threshold multiplier, and the interquartile range; and determine the normalized metric value is an outlier based on the normalized metric value being greater than the upper limit of the threshold or less than the lower limit of the threshold.

13. The system of claim 12, where in the at least one processor is further configured to:

determine one of the lower limit of the threshold or the upper limit of the threshold is less than a degradation value; and in response to the determining, increase one of the lower limit of the threshold or the upper limit of the threshold by a degradation factor.

14. The system of claim 11, wherein the at least one processor is further configured to:

update a permission associated with a medical device, wherein the updated permission is configured to prevent access by the provider.

15. The system of claim 11, wherein the at least one processor is further configured to:

retrieve the code from the first claim;

transmit a request for the specialty group to a data provider system, the request including the code and the provider;

receive the specialty group from the data provider system; and assign the provider to the specialty group.

16. The system of claim 11, wherein the alert includes a link to access a graphical user interface providing additional information associated with the alert.

17. The system of claim 11, wherein the metric is one of mortality rate, length of stay, readmission rate, audit rate, average total charges value, denial rate, or medicine prescription rate.

18. A non-transitory computer-readable device having instructions stored thereon that, when executed by at least one computing device, cause the at least one computing device to perform operations comprising:

receiving a first claim including a provider, an illness, a treatment, a code, and a risk score, wherein the risk score is based on the illness and the treatment;

in real-time in response to receiving the first claim:

grouping, based on the code, the provider into a specialty group;

updating a metric associated with the provider based on the first claim;

computing, based on historical risk score and metric data of the specialty group corresponding to a dynamic rolling time window, a risk impact coefficient, wherein the risk impact coefficient represents a linear relationship between the metric and the risk score;

determining an impact of the risk score based on the risk impact coefficient and the risk score;

subtracting the impact of the risk score from the metric to generate a normalized metric value;

determining that the normalized metric value is an outlier by:

comparing the normalized metric value to a threshold corresponding to the specialty group; and determining, based on the specialty group, that the normalized metric value is associated with a statistically significant number of claims; and in response to determining that the normalized metric value is an outlier, transmitting an alert to a client device associated with a user, wherein the alert is configured to cause a display of the client device to display an indication of the outlier.

19. The non-transitory computer-readable device of claim 18, wherein when comparing the normalized metric value to the threshold, the operations further comprise:

generating a first quartile value and a second quartile value based on a plurality of normalized metric values corresponding to a plurality of providers of the specialty group;

determining an interquartile range based on the first quartile value and the second quartile value;

calculating a median value of the interquartile range;

calculating a lower limit of the threshold based on the median value, a threshold multiplier, and the interquartile range;

calculating an upper limit of the threshold based on the median value, the threshold multiplier, and the interquartile range; and determining the normalized metric value is an outlier based on the normalized metric value being greater than the upper limit of the threshold or less than the lower limit of the threshold.

20. The non-transitory computer-readable device of claim 19, the operations further comprising:

determining one of the lower limit of the threshold or the upper limit of the threshold is less than a degradation value; and in response to the determining, increasing one of the lower limit of the threshold or the upper limit of the threshold by a degradation factor.

* * * * *